US012629131B2

(12) United States Patent
Kim et al.

(10) Patent No.: US 12,629,131 B2
(45) Date of Patent: May 19, 2026

(54) ULTRASONIC PROBE COMPRISING CONNECTORS AND COUPLERS AND METHOD FOR MANUFACTURING SAME

(71) Applicant: Samsung Medison Co., Ltd., Hongcheon-gun (KR)

(72) Inventors: Yoon Seok Kim, Hongcheon-gun (KR); Min Yeol Yoon, Hongcheon-gun (KR)

(73) Assignee: SAMSUNG MEDISON CO., LTD., Hongcheon-Gun (KR)

( * ) Notice: Subject to any disclaimer, the term of this patent is extended or adjusted under 35 U.S.C. 154(b) by 63 days.

(21) Appl. No.: 18/282,212

(22) PCT Filed: Aug. 20, 2021

(86) PCT No.: PCT/KR2021/011148
§ 371 (c)(1),
(2) Date: Sep. 14, 2023

(87) PCT Pub. No.: WO2022/196872
PCT Pub. Date: Sep. 22, 2022

(65) Prior Publication Data
US 2024/0156432 A1 May 16, 2024

(30) Foreign Application Priority Data
Mar. 16, 2021 (KR) ........................ 10-2021-0034293

(51) Int. Cl.
*A61B 8/00* (2006.01)
(52) U.S. Cl.
CPC ................................... *A61B 8/4444* (2013.01)
(58) Field of Classification Search
CPC ... A61B 8/4444; A61B 8/4405; A61B 8/4461; A61B 8/4483; A61B 8/4455; A61B 2560/0406; A61B 2562/12; A61B 2562/16
See application file for complete search history.

(56) References Cited

U.S. PATENT DOCUMENTS

| | | | | |
|---|---|---|---|---|
| 5,176,140 A | * | 1/1993 | Kami | .................... B06B 1/0644 |
| | | | | 600/459 |
| 7,905,844 B2 | | 3/2011 | Desilets et al. | |

(Continued)

FOREIGN PATENT DOCUMENTS

| | | |
|---|---|---|
| CN | 204500763 U | 7/2015 |
| CN | 208926425 U | 6/2019 |

(Continued)

OTHER PUBLICATIONS

International Search Report and Written Opinion issued in corresponding International Application No. PCT/KR2021/011148 dated Dec. 13, 2021, with English translation.

(Continued)

*Primary Examiner* — Joel Lamprecht
*Assistant Examiner* — James F Mcdonald, III
(74) *Attorney, Agent, or Firm* — Morgan Lewis & Bockius LLP

(57) ABSTRACT

According to an embodiment of the disclosure, an ultrasonic probe may be provided, the ultrasonic probe including a first housing, a second housing coupled to the first housing, an acoustic module at least partially arranged in the first housing and including a transducer and a lens portion, the transducer being capable of converting an ultrasonic signal and an electrical signal, and the lens portion being capable of changing a path of the ultrasonic signal, a first connector connected to an inner surface of the first housing, and a second connector at least partially arranged in the second housing and connected to the first connector, wherein the first connector is configured to connect the second connector and the first housing to each other, such that the first housing is coupled to the second housing.

14 Claims, 10 Drawing Sheets

(56)                References Cited

U.S. PATENT DOCUMENTS

| 10,085,717 | B2 | 10/2018 | Cho et al. | |
| 2002/0038088 | A1* | 3/2002 | Imran | A61B 8/08 |
| | | | | 600/443 |
| 2003/0220573 | A1* | 11/2003 | Imran | A61B 8/467 |
| | | | | 600/459 |
| 2004/0073118 | A1* | 4/2004 | Peszynski | A61B 8/12 |
| | | | | 600/459 |
| 2005/0165313 | A1 | 7/2005 | Byron et al. | |
| 2006/0241467 | A1* | 10/2006 | Takeda | G10K 9/18 |
| | | | | 600/459 |
| 2008/0188756 | A1* | 8/2008 | Fujimura | A61B 8/445 |
| | | | | 600/459 |
| 2012/0046551 | A1 | 2/2012 | Tang | |
| 2013/0226004 | A1 | 8/2013 | Lee | |
| 2013/0253327 | A1* | 9/2013 | Ko | A61B 8/4444 |
| | | | | 600/459 |
| 2013/0301395 | A1 | 11/2013 | Hebrard et al. | |
| 2015/0112201 | A1* | 4/2015 | Nakanishi | A61B 8/4411 |
| | | | | 600/472 |
| 2018/0125461 | A1 | 5/2018 | Clark et al. | |
| 2019/0133823 | A1* | 5/2019 | Banko | A61F 9/00745 |
| 2019/0231311 | A1* | 8/2019 | Kwon | G01N 29/2406 |
| 2020/0093463 | A1 | 3/2020 | Sams et al. | |

FOREIGN PATENT DOCUMENTS

| EP | 2124752 B1 * | 4/2019 | | A61B 8/00 |
| JP | 2018-517439 A | 7/2018 | | |
| KR | 10-0455606 B1 | 11/2004 | | |
| KR | 10-2010-0050845 A | 5/2010 | | |
| KR | 10-1387934 B1 | 4/2014 | | |
| KR | 10-2016-0018235 A | 2/2016 | | |
| KR | 10-2019-0035263 A | 4/2019 | | |
| WO | 2014/080312 A1 | 5/2014 | | |

OTHER PUBLICATIONS

Extended European Search Report dated Feb. 25, 2025 issued in corresponding European Patent Application No. 21931815.1.
European Notice of Allowance dated Jul. 28, 2025 issued in European Patent Application No. 21931815.1.
Office Action dated Nov. 13, 2025 issued in the corresponding Korean Patent Application No. 10-2021-0034293 with the English translation.

* cited by examiner

ULTRASONIC PROBE COMPRISING CONNECTORS AND COUPLERS AND METHOD FOR MANUFACTURING SAME

This application is a National Phase application of International Application No. PCT/KR2021/011148 dated Aug. 20, 2021, which claims priority to Korean Patent Application No. 10-2021-0034293 filed on Mar. 16, 2021, the entire contents of each are hereby incorporated by reference.

TECHNICAL FIELD

The disclosure relates to an ultrasonic probe and a method of manufacturing the same, and more particularly, to an ultrasonic probe, which is configured so that damage to components of the ultrasonic probe is prevented and assembly and disassembly of the ultrasonic probe are facilitated, and to a method of manufacturing the ultrasonic probe.

BACKGROUND ART

An ultrasonic diagnosis apparatus refers to an apparatus capable of providing an ultrasonic signal to a target region in the body of an object, and obtaining biometric information about the object, based on information about the reflected ultrasonic signal. When compared with other imaging diagnosis apparatuses such as an X-ray diagnosis apparatus, ultrasonic diagnosis apparatuses are inexpensive and have little impact on an object. In particular, according to an embodiment, the ultrasonic diagnosis apparatus may include an ultrasonic probe that can be easily operated by a user.

The ultrasonic probe includes a component capable of outputting an ultrasonic signal and includes a lens assembly configured to appropriately change a path of the ultrasonic signal. In order to manufacture an ultrasonic probe, an assembly process for individual components such as a housing constituting the ultrasonic probe is required. In this case, there is a need to prevent damage to the component capable of outputting the ultrasonic signal and the lens assembly while the assembly process is performed. Accordingly, research into the ultrasonic probe capable of reducing damage or impact on components included in the ultrasonic probe has been continuously conducted.

DISCLOSURE

Technical Problem

A technical problem of the disclosure is to provide an ultrasonic probe and a method of manufacturing the same, in which damage to components of the ultrasonic probe is prevented during a manufacturing process of the ultrasonic probe.

Another technical problem of the disclosure is to provide an ultrasonic probe and a method of manufacturing the same, in which internal components of the ultrasonic probe may be engaged with or separated from each other according to a selection of a user, such that accessibility to the internal components is improved.

The technical problems of the disclosure are not limited to the problems mentioned above, and other technical problems not mentioned above will be clearly understood by those of ordinary skill in the art from the description below.

Technical Solution

According to an embodiment of the disclosure, an ultrasonic probe may be provided, the ultrasonic probe including a first housing, a second housing coupled to the first housing, an acoustic module at least partially arranged in the first housing and including a transducer and a lens portion, the transducer being capable of converting an ultrasonic signal and an electrical signal, and the lens portion being capable of changing a path of the ultrasonic signal, a first connector connected to an inner surface of the first housing, and a second connector at least partially arranged in the second housing and connected to the first connector, wherein the first connector is configured to connect the second connector and the first housing to each other, such that the first housing is coupled to the second housing.

According to an embodiment, the first housing and the second housing may be physically in contact with each other without an adhesive member therebetween.

According to an embodiment, the first connector may not be directly connected to the lens portion.

According to an embodiment, when the second connector applies an external force to the first connector in a first direction, the first connector may be configured to apply an external force to the first housing in the first direction.

According to an embodiment, the first connector and the first housing may be integrally formed.

According to an embodiment, the second connector may include a main body portion accommodated in the second housing and a branch portion extending from the main body portion, the main body portion may extend in a longitudinal direction of the second housing, the branch portion may be engaged with the first connector, and a number of the branch portion may be equal to a number of the first connector.

According to an embodiment, the ultrasonic probe may further include a coupler capable of changing relative positions of the second connector and the second housing with respect to each other, wherein the second housing may be between the first housing and the coupler.

According to an embodiment, the coupler may include a first coupler and a second coupler, the second coupler being configured to be engaged with or separated from the first coupler.

According to an embodiment, the first coupler may be configured to connect the second connector to the second coupler and may be insertable into the second coupler.

According to an embodiment, the ultrasonic probe may include a head position where the acoustic module is arranged and a tail position where the coupler is arranged, and when the first coupler and the second coupler are engaged with each other, the first coupler may be configured to pull the second connector in a rearward direction, wherein the rearward direction may be a direction from the head position toward the tail position.

According to an embodiment, when the first coupler and the second coupler are engaged with each other, the second connector may be configured to pull the first connector in the rearward direction, and the first connector may be configured to pull the first housing in the rearward direction.

According to an embodiment, when the first coupler and the second coupler are engaged with each other, the second coupler may be configured to push the second housing in a forward direction, wherein the forward direction may be a direction from the tail position toward the head position.

According to an embodiment, when the first coupler and the second coupler are engaged with each other, an external force may be applied to the second housing in the forward direction, and an external force may be applied to the first housing in the rearward direction.

According to an embodiment, when the first coupler is inserted into the second coupler by a certain height, the first coupler and the second coupler may be arranged at a critical engagement position, and when the first coupler and the second coupler are arranged at the critical engagement position, the first housing and the second housing may form a contact surface with each other, and movement of each of the first housing and the second housing may be limited.

According to an embodiment, when the first coupler and the second coupler are arranged at the critical engagement position, one end of the second housing may be connected to the first housing, and the other end of the second housing may be connected to the second coupler.

According to an embodiment, the ultrasonic probe may further include a first O-ring between the first housing and the second housing, and a second O-ring between the second housing and the first coupler.

According to an embodiment, the second O-ring may be in contact with the first coupler without contacting the second coupler.

According to another embodiment of the disclosure, a method of manufacturing an ultrasonic probe may be provided, the method including preparing a first module and a second module, wherein the first module includes a first housing, an acoustic module at least partially arranged in the first housing, a first connector connected to an inner surface of the first housing, a second connector connected to the first connector, and a first coupler connected to the second connector, and the second module includes a second housing capable of accommodating at least a portion of the second connector, and a second coupler configured to be engaged with or separated from the first coupler, arranging the second connector to be accommodated in the second housing, and engaging the first coupler and the second coupler to each other, wherein the first connector is configured to connect the second connector and the first housing to each other, such that the first housing is coupled to the second housing.

According to an embodiment, the method may further include changing the first module and the second module from a disengaged state to an engaged state, and changing the first module and the second module from the engaged state to the disengaged state, wherein the engaged state may be a state in which one end of the second housing is connected to the first housing and the other end of the second housing is connected to the second coupler, and the disengaged state may be a state in which the first coupler and the second coupler are not engaged with each other.

According to an embodiment, the method may further include pulling, by the second connector, the first housing in a rearward direction through the first connector, and pushing, by the second coupler, the second housing in a forward direction, wherein the forward direction may be a direction from a position where the second coupler is arranged toward a position where the acoustic module is arranged, and the rearward direction may be a direction from the position where the acoustic module is arranged to the direction where the second coupler is arranged.

According to an embodiment, the engaging of the first coupler and the second coupler to each other may further include applying, by the second connector, an external force to the first connector in a first direction, and applying, by the first connector, an external force to the first housing in the first direction.

The technical solutions of the disclosure are not limited to the above technical solutions, and other technical solutions not mentioned herein will be clearly understood by those of ordinary skill in the art from the present specification and the accompanying drawings.

Advantageous Effects

According to an embodiment of the disclosure, there may be provided an ultrasonic probe and a method of manufacturing the same, in which damage to components of the ultrasonic probe is prevented during a manufacturing process of the ultrasonic probe.

According to another embodiment of the disclosure, there may be provided an ultrasonic probe and a method of manufacturing the same, in which internal components of the ultrasonic probe may be engaged with or separated from each other according to a selection of a user, such that accessibility to the internal components is improved.

The advantages and effects of the disclosure are not limited to the above advantages and effects, and other advantages and effects not mentioned herein will be clearly understood by those of ordinary skill in the art from the present specification and the accompanying drawings.

Figure 2:
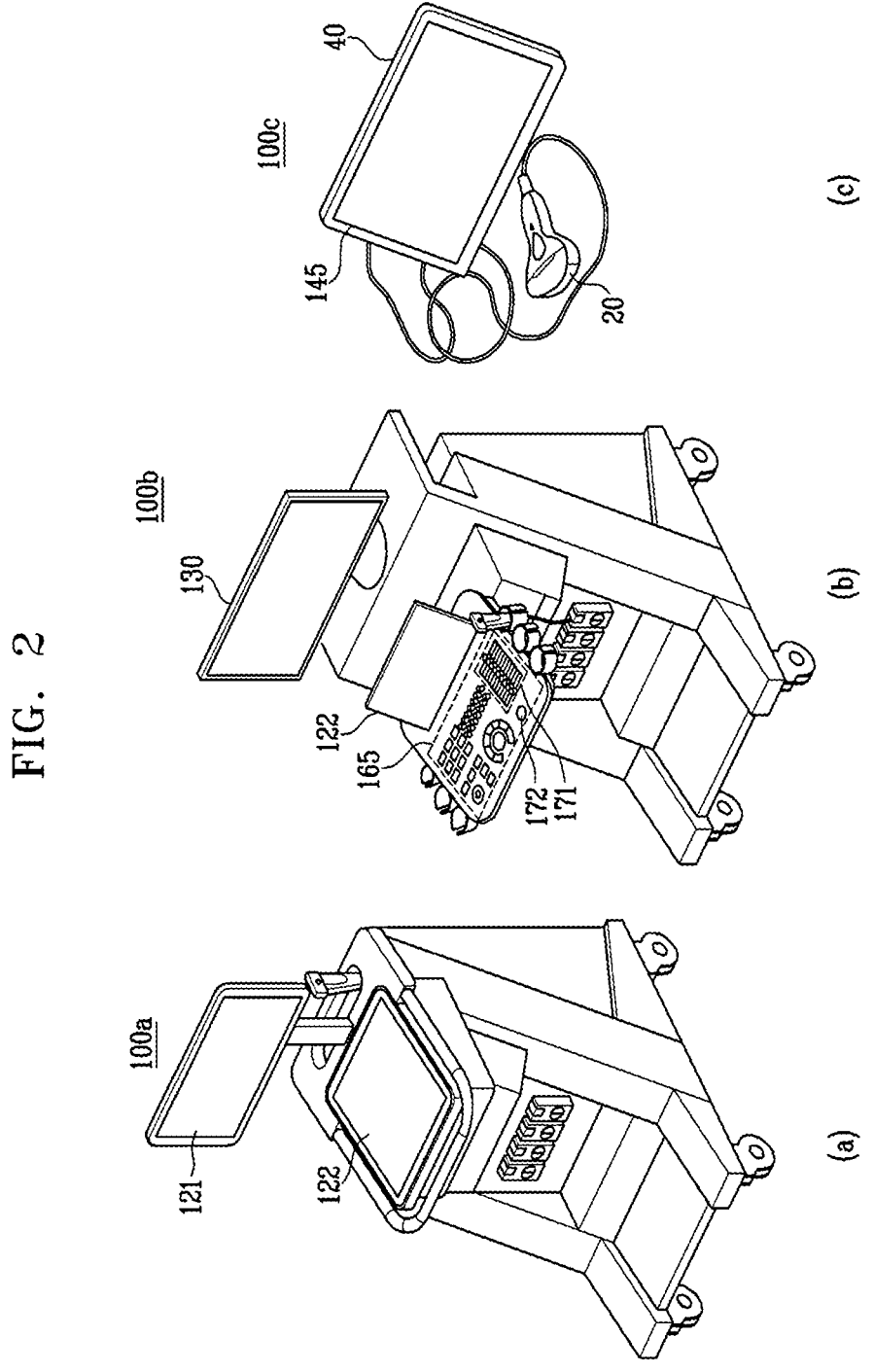

(a) to (c) of FIG. 2 are diagrams of an ultrasonic diagnosis apparatus according to an embodiment.

Figure 3:
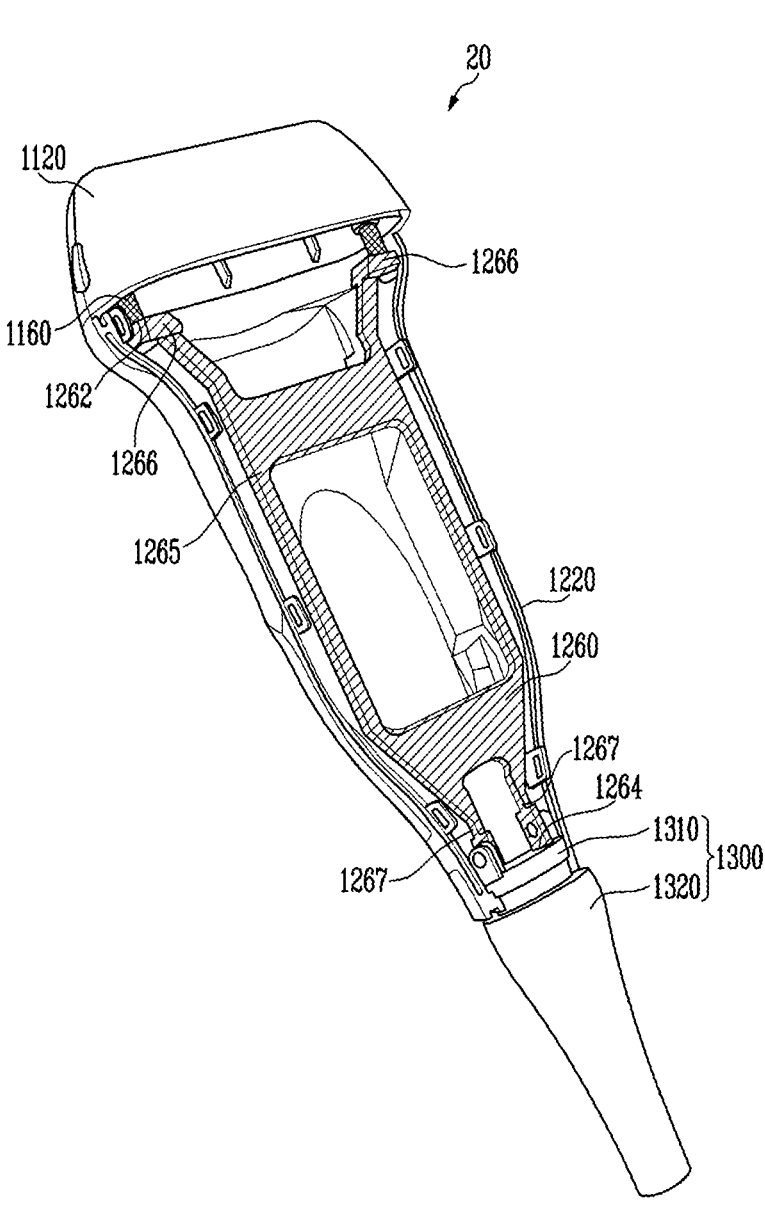

FIG. 3 is a perspective view of an ultrasonic probe according to an embodiment.

Figure 4:
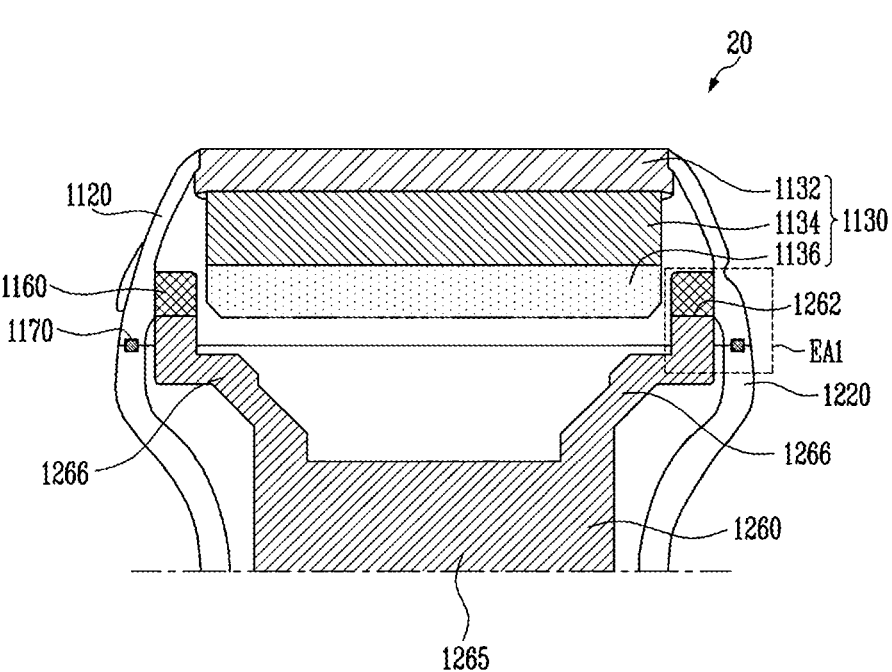

FIG. 4 is a cross-sectional view of an ultrasonic probe according to an embodiment.

Figure 5:
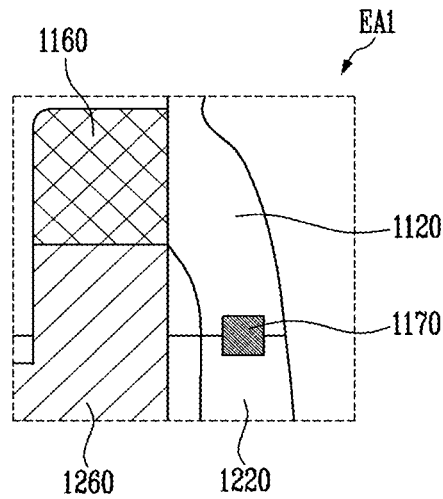

FIG. 5 is an enlarged view of a region EA1 of FIG. 4.

Figure 6:
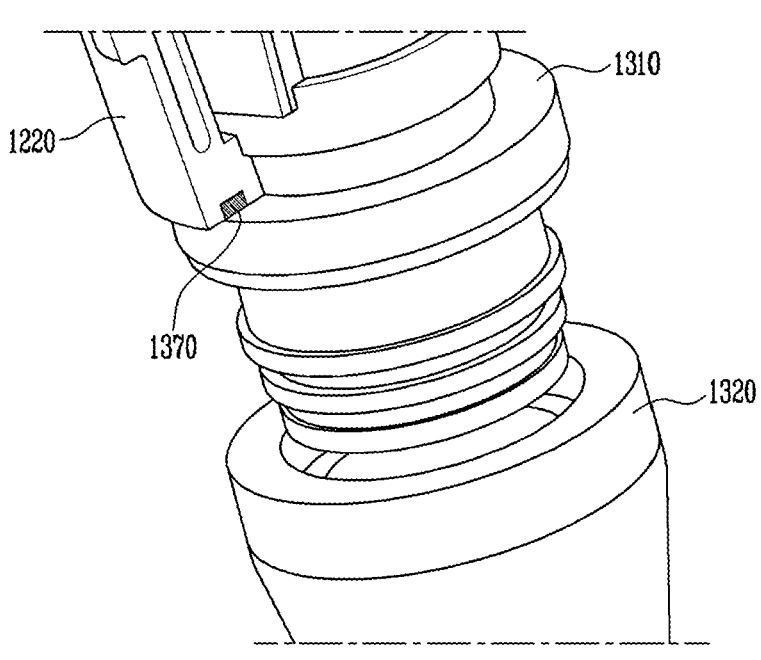

FIG. 6 is a schematic perspective view of a coupling between a first coupler and a second coupler, according to an embodiment.

Figure 7:
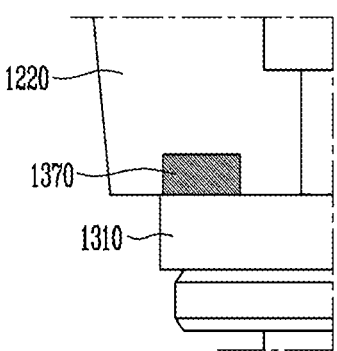

FIG. 7 is a schematic perspective view of a first coupler and a second housing, according to an embodiment.

Figure 8:
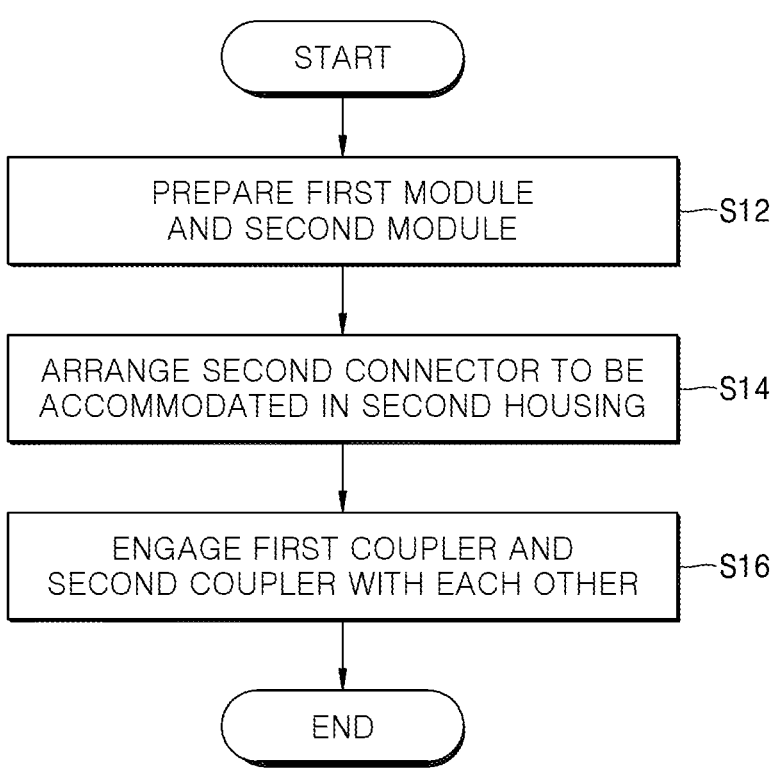

FIG. 8 is a flowchart of a method of manufacturing an ultrasonic probe, according to an embodiment.

Figure 9:
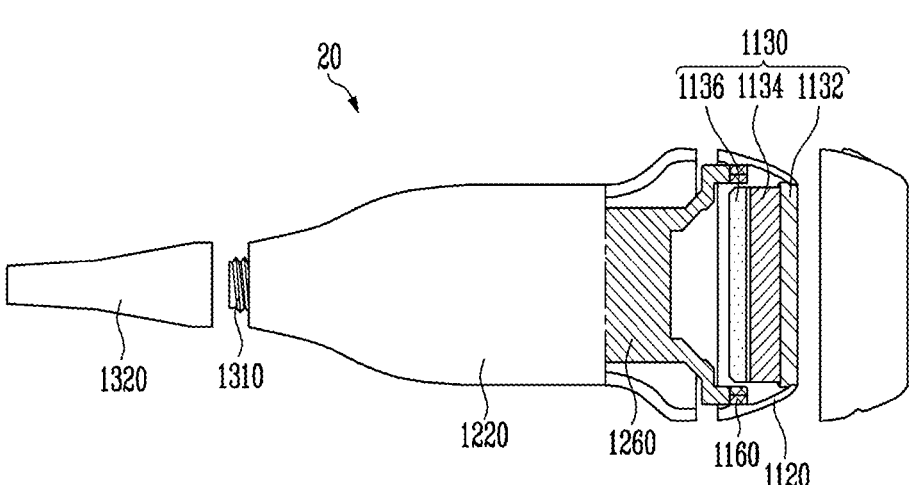
Figure 10:
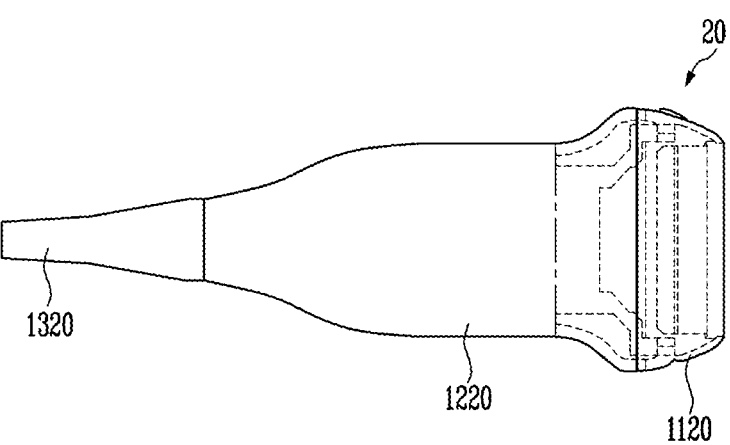

FIGS. 9 and 10 are diagrams for respective manufacturing operations of a method of manufacturing an ultrasonic probe, according to an embodiment.

MODE FOR INVENTION

The specification clarifies the scope of the disclosure, and the principles and embodiments of the disclosure are described and set forth herein, such that those of ordinary skill in the art can practice the embodiments of the disclosure. The embodiments of the disclosure may be implemented in various forms.

Throughout the specification, when a component is referred to as being "connected" to another component, it may be not only directly connected to the other component, but also indirectly connected to the other component, and the indirect connection may be made through a wireless communication network.

Also, terms used herein are used to describe the embodiments and are not intended to limit the embodiments set forth herein. An expression used in the singular encompasses the expression in the plural, unless it has a clearly different meaning in the context. The terms "comprise" or "include" used herein are intended to specify the presence of features, numbers, steps, operations, components, parts, or combinations thereof set forth herein and do not preclude the presence or addition of one or more other features, numbers, steps, operations, components, parts, or combinations thereof.

In addition, the terms including ordinal numbers such as "first" and "second" used herein may be used to describe various components. However, the components are not limited by the terms, and the terms are used only for the purpose of distinguishing one component from another. For example, a first component may be referred to as a second component, and similarly, a second component may be referred to as a first component, without departing from the scope of the disclosure.

Also, the terms " . . . or/er", "group", "block", "member", "module", or the like may refer to a unit that processes at least one function or operation. For example, the above terms may refer to at least one hardware such as a field-programmable gate array (FPGA)/application specific integrated circuit (ASIC), at least one software stored in a memory, or at least one process processed by a processor.

Reference numerals assigned to operations are used to identify the operations and do not indicate the order of the operations. The operations may be performed in a different order from a specified order unless a specific order is explicitly described in context.

Also, as used herein, an image may include a medical image obtained by a medical imaging apparatus such as a magnetic resonance imaging (MRI) apparatus, a computed tomography (CT) apparatus, an ultrasound imaging apparatus, or an X-ray imaging apparatus.

In addition, as used herein, an "object" is an object to be photographed and may include a human, an animal, or a part thereof. For example, the object may include a body part (such as an organ) or a phantom.

Throughout the specification, an "ultrasound image" refers to an image of an object that is processed based on an ultrasonic signal transmitted to the object and reflected from the object.

Hereinafter, an ultrasonic probe and a method of manufacturing the same according to embodiments will be described in detail with reference to FIGS. 1 to 10.

Figure 1:
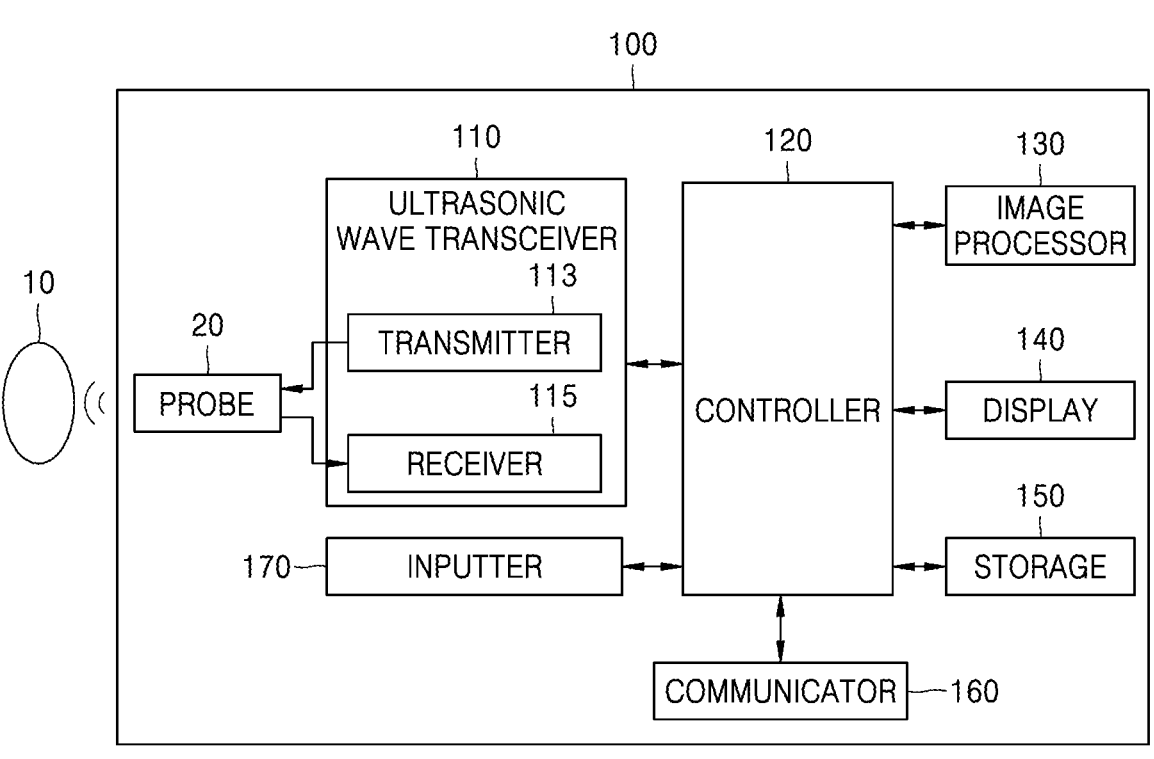
FIG. 1 is a block diagram of a configuration of an ultrasonic diagnosis apparatus according to an embodiment.

FIG. 1 is a block diagram of a configuration of an ultrasonic diagnosis apparatus according to an embodiment. An ultrasonic diagnosis apparatus 100 according to an embodiment may include a probe 20, an ultrasonic wave transceiver 110, a controller 120, an image processor 130, a display 140, a storage 150, a communicator 160, and an inputter 170.

The ultrasonic diagnosis apparatus 100 may be implemented as a cart-type ultrasonic diagnosis apparatus and a portable ultrasonic diagnosis apparatus. Examples of a portable ultrasonic diagnosis apparatus may include a smartphone, a laptop computer, a personal digital assistance (PDA), and a tablet personal computer (PC), but are not limited thereto.

The probe 20 may include a plurality of transducers 1134 (see FIG. 4). The plurality of transducers 1134 may transmit an ultrasonic signal to an object 10 according to a transmission signal applied from a transmitter 113. The plurality of transducers 1134 may form a reception signal by receiving the ultrasonic signal reflected from the object 10. Also, the probe 20 may be integrally implemented with the ultrasonic diagnosis apparatus 100 or implemented as a separate probe connected to the ultrasonic diagnosis apparatus 100 by wire or wirelessly. In addition, the ultrasonic diagnosis apparatus 100 may include one or a plurality of probes 20 according to an implementation form. According to an embodiment, the probe 20 may be referred to as an ultrasonic probe 20.

The controller 120 controls the transmitter 113 to form a transmission signal to be applied to each of the plurality of transducers 1134 in consideration of positions and focal points of the plurality of transducers 1134 included in the probe 20.

The controller 120 controls a receiver 115 to generate ultrasound data by performing analog-to-digital conversion of reception signals received from the probe 20 and summing the digitally converted reception signals in consideration of the positions and focal points of the plurality of transducers 1134.

The image processor 130 generates an ultrasound image by using the ultrasound data generated by the receiver 115.

The display 140 may display the generated ultrasound image and various types of information processed by the ultrasonic diagnosis apparatus 100. The ultrasonic diagnosis apparatus 100 may include one or a plurality of displays 140 according to an implementation form. Also, the display 140 may be combined with a touch panel to be implemented as a touch screen.

The controller 120 may control overall operations of the ultrasonic diagnosis apparatus 100 and signal flows between internal components of the ultrasonic diagnosis apparatus 100. The controller 120 may include a memory storing programs or data for performing functions of the ultrasonic diagnosis apparatus 100, and a processor that processes the programs or data. Also, the controller 120 may control the operation of the ultrasonic diagnosis apparatus 100 by receiving a control signal from the inputter 170 or an external apparatus.

The ultrasonic diagnosis apparatus 100 includes the communicator 160 and may be connected to the external apparatus through the communicator 160 (e.g., a server, a medical apparatus, a portable apparatus (smartphone, tablet PC, wearable device, etc.), or the like).

The communicator 160 may include one or more components that enable communication with the external apparatus and may include, for example, at least one of a short-distance communication module, a wired communication module, and a wireless communication module.

The communicator 160 may receive a control signal and data from the external apparatus, transmit the received control signal to the controller 120, and allow the controller 120 to control the ultrasonic diagnosis apparatus 100 according to the received control signal.

Alternatively, the controller 120 may transmit a control signal to the external apparatus through the communicator 160 to control the external apparatus according to the control signal of the controller.

For example, the external apparatus may process data of the external apparatus according to the control signal of the controller, the control signal being received through the communicator.

A program (artificial intelligence, etc.) capable of controlling the ultrasonic diagnosis apparatus 100 may be installed on the external apparatus, and this program may include instructions for performing some or all of the operations of the controller 120.

The program may be pre-installed on the external apparatus, or a user of the external apparatus may download and install the program from a server providing the application. The server providing the application may include a recording medium having the corresponding program stored therein.

Also, in a system including a server and a client apparatus, the program may include a storage medium of the server or a storage medium of the client apparatus. Alternatively, when there is a third apparatus (smartphone, tablet PC, wearable device, etc.) communicatively connected to the server or the client apparatus, a program product may include a storage medium of the third apparatus. Alternatively, the program may include an SAN program itself, which is transmitted from the server to the client apparatus or the third apparatus or transmitted from the third apparatus to the client apparatus.

In this case, one of the server, the client apparatus, and the third apparatus may execute the program to perform the method according to the embodiments of the disclosure. Alternatively, two or more of the server, the client apparatus, and the third apparatus may execute the program to perform the method according to the embodiments of the disclosure in a distributed manner.

For example, the server (e.g., a cloud server or an artificial intelligence server) may execute the program stored in the server to control the client apparatus to perform the method according to the embodiments of the disclosure, the client apparatus being communicatively connected to the server.

The storage 150 may store various pieces of data or programs for driving and controlling the ultrasonic diagnosis apparatus 100, input/output ultrasound data, an obtained ultrasound image, or the like.

The inputter 170 may receive a user input for controlling the ultrasonic diagnosis apparatus 100. For example, the user input may include an input for operating a button, a keypad, a mouse, a trackball, a jog switch, a knob, etc., an input for touching a touch pad or a touch screen, a speech input, a motion input, a biometric information input (e.g., iris recognition, fingerprint recognition, etc.), or the like, but is not limited thereto.

Examples of the ultrasonic diagnosis apparatus 100 according to an embodiment will be described below with reference to (a) to (c) of FIG. 2.

(a) to (c) of FIG. 2 are diagrams of an ultrasonic diagnosis apparatus according to an embodiment.

Referring to (a) and (b) of FIG. 2, ultrasonic diagnosis apparatuses 100a and 100b may each include a main display 121 and a sub-display 122. One of the main display 121 and the sub-display 122 may be implemented as a touch screen. The main display 121 and the sub-display 122 may display ultrasound images or various pieces of information processed by the ultrasonic diagnosis apparatuses 100a and 100b. Also, the main display 121 and the sub-display 122 are implemented as touch screens, and may provide a graphical user interface (GUI) to receive an input of data for controlling the ultrasonic diagnosis apparatuses 100a and 100b from a user. For example, the main display 121 may display an ultrasound image, and the sub-display 122 may display a control panel for controlling the display of the ultrasound image in the form of a GUI. The sub-display 122 may receive an input of data for controlling the display of an image through the control panel displayed in the form of the GUI. The ultrasonic diagnosis apparatuses 100a and 100b may control the display of the ultrasound image displayed on the main display 121 by using input control data.

Referring to (b) of FIG. 2, the ultrasonic diagnosis apparatus 100b may further include a control panel 165 in addition to the main display 121 and the sub-display 122. The control panel 165 may include a button, a trackball, a jog switch, a knob, etc. and receive an input of data for controlling the ultrasonic diagnosis apparatus 100b from a user. For example, the control panel 165 may include a time gain compensation (TGC) button 171, a freeze button 172, or the like. The TGC button 171 is a button for selecting a TGC value for each depth of an ultrasound image. Also, when an input of the freeze button 172 is detected while scanning the ultrasound image, the ultrasonic diagnosis apparatus 100b may maintain a state in which a frame image at a corresponding time point is displayed.

In addition, the button, trackball, jog switch, knob, etc. included in the control panel 165 may be provided as a GUI on the main display 121 or the sub-display 122.

Referring to (c) of FIG. 2, an ultrasonic diagnosis apparatus 100c may also be implemented as a portable ultrasonic diagnosis apparatus. Examples of the portable ultrasonic diagnosis apparatus 100c may include a smartphone, a laptop computer, a PDA, a tablet PC, etc. including a probe and an application, but are not limited thereto.

The ultrasonic diagnosis apparatus 100c may include a probe 20 and a main body 40, and the probe 20 may be connected to one side of the main body 40 by wire or wirelessly. The main body 40 may include a touch screen 145. The touch screen 145 may display ultrasound images, various pieces of information processed by the ultrasonic diagnosis apparatus, and a GUI.

In addition, the embodiments of the disclosure may be implemented in the form of a recording medium storing instructions executable by a computer. The instructions may be stored in the form of program codes, and when executed by a processor, may generate a program module to perform operations of the embodiments of the disclosure. A recording medium may be implemented as a computer-readable recording medium.

The computer-readable recording medium may include all types of recording media stored therein instructions decodable by a computer. For example, the computer-readable recording medium may include read-only memory (ROM), random access memory (RAM), a magnetic tape, a magnetic disk, a flash memory, an optical data storage apparatus, etc.

Hereinafter, an ultrasonic probe 20 according to an embodiment will be described in more detail with reference to FIGS. 3 to 7.

FIG. 3 is a perspective view of an ultrasonic probe according to an embodiment. FIG. 4 is a cross-sectional view of an ultrasonic probe according to an embodiment. In FIG. 4, a first housing 1120 and components arranged adjacent to the first housing 1120 in the ultrasonic probe according to an embodiment are mainly described.

According to an embodiment, the ultrasonic probe 20 may include a one-dimensional (1D) array probe, a two-dimensional (2D) array probe, or a three-dimensional (3D) array probe, but is not limited to a specific example.

Referring to FIGS. 3 and 4, the ultrasonic probe 20 according to an embodiment may include the first housing 1120, an acoustic module 1130, a first connector 1160, a first O-ring 1170, a second housing 1220, a second connector 1260, and a coupler 1300. According to an embodiment, the acoustic module 1130 may include a lens portion 1132, a transducer 1134, and a sound absorber 1136. The coupler 1300 may include a first coupler 1310 and a second coupler 1320.

The first housing 1120 may support an external shape of the ultrasonic probe 20. The first housing 1120 may provide a space capable of accommodating the lens portion 1132, the transducer 1134, and/or the sound absorber 1136. The first housing 1120 may protect the acoustic module 1130 from external impacts. According to an embodiment, the first housing 1120 may be referred to as a head housing.

According to an embodiment, at least a portion of the first housing 1120 may be connected to the acoustic module 1130. At least a portion of the first housing 1120 may be connected to the lens portion 1132. According to an embodiment, the first housing 1120 may include an opening to expose the lens portion 1132 to the outside. The portion of the first housing 1120 forming the opening may be physically in contact with the lens portion 1132.

According to an embodiment, the first housing 1120 may be connected to the first connector 1160. An inner surface of the first housing 1120 may form a contact surface with the first connector 1160. The inner surface of the first housing 1120 may be in contact with the first connector 1160.

According to an embodiment, the first housing 1120 may include a cavity (or groove), and the first O-ring 1170 may be accommodated in the cavity. The cavity may be arranged adjacent to a contact surface between the first housing 1120 and the second housing 1220.

According to an embodiment, the first housing 1120 may be coupled to the second housing 1220. The first housing 1120 and the second housing 1220 may form a contact surface having a certain shape. The first housing 1120 and the second housing 1220 may be physically in contact with each other without an adhesive member between. The first housing 1120 and the second housing 1220 may be coupled to each other, and an inner area of the ultrasonic probe 20 may be separated from the outside.

The acoustic module 1130 may be arranged in the first housing 1120. The acoustic module 1130 may receive an echo signal reflected from the object 10. The reflected echo signal may be an ultrasonic signal reflected from the object 10.

The lens portion 1132 may be provided in the first housing 1120. The lens portion 1132 may be physically connected to the first housing 1120. The lens portion 1132 may be arranged in the opening formed in the first housing 1120. The lens portion 1132 may be arranged on one surface of the transducer 1134.

According to an embodiment, the lens portion 1132 may change a heading direction of the ultrasonic signal emitted from the transducer 1134.

The transducer 1134 may be provided in the first housing 1120. The transducers 1134 may be between the lens portion 1132 and the sound absorber 1136.

According to an embodiment, the transducer 1134 may be provided as a plurality of transducers and receive an electrical signal. The transducer 1134 may convert an ultrasonic signal and an electrical signal into each other. According to an embodiment, the transducer 1134 may vibrate according to the transmitted electrical signal, emit an ultrasonic signal that is acoustic energy, and obtain an electrical signal by processing the acoustic energy reflected from the object 10.

The sound absorber 1136 may be provided in the first housing 1120. The sound absorber 1136 may be arranged on the other surface of the transducer 1134.

According to an embodiment, the sound absorber 1136 may be arranged on the lower surface of the transducer 1134 to block ultrasonic waves emitted from the transducer 1134 from traveling rearward, not in a direction in which the lens portion 1132 is arranged. According to an embodiment, the sound absorber 1136 may include a plurality of layers, but is not limited to a specific example. Various well-known structures may be applied to the sound absorber 1136 to improve the performance of blocking ultrasonic waves.

At least a portion of the first connector 1160 may be arranged in the first housing 1120. The first connector 1160 may be accommodated in the first housing 1120 and be physically in contact with the first housing 1120. The first connector 1160 may not be directly connected to the lens portion 1132.

According to an embodiment, the first connector 1160 may be physically connected to the inner surface of the first housing 1120. The first connector 1160 may be coupled to the second connector 1260. Accordingly, the first connector 1160 may connect the first housing 1120 to the second connector 1260. According to an embodiment, when the second connector 1260 applies an external force to the first connector 1160 in a first direction, the first connector 1160 may apply an external force to the first housing 1120 in the first direction.

According to an embodiment, the first connector 1160 may be separately provided, and assembled and provided with the first housing 1120. However, a method of forming the first connector 1160 is not limited to the aforementioned example. According to an embodiment, the first connector 1160 may be integrally formed with the first housing 1120. In this case, the first connector 1160 may be injection-molded and formed in the same process as the first housing 1120.

According to an embodiment, the first connector 1160 may include a rigid material. The first connector 1160 may include metal or plastic, but is not limited to a specific example.

According to an embodiment, the first connector 1160 may be provided as a plurality of first connectors. For example, as shown in FIGS. 3 and 4, two first connectors 1160 may be provided. One of the first connectors 1160 may be connected to a left inner surface of the first housing 1120, and the other of the first connectors 1160 may be connected to a right inner surface of the first housing 1120. However, the number of first connectors 1160 is not limited to the aforementioned example.

According to an embodiment, the first connector 1160 may not be connected to the second housing 1220. The first connector 1160 may not be physically in contact with the second housing 1220.

The O-ring 1170 may be between the first housing 1120 and the second housing 1220. A structure of the first O-ring 1170 is described with reference to FIG. 5. FIG. 5 is an enlarged view of a region EA1 of FIG. 4. Referring to FIG. 5, because the first O-ring 1170 may be positioned in a space defined by a cavity (or groove) of each of the first housing 1120 and the second housing 1220 to prevent gaps from occurring between the first housing 1120 and the second housing 1220 and to maximize sealing performance.

The second housing 1220 may support an external shape of the ultrasonic probe 20. The second housing 1220 may be between the first housing 1120 and the coupler 1300. The second housing 1220 may be referred to as a tail housing or a handle housing.

According to an embodiment, the second housing 1220 may provide a space capable of accommodating the second connector 1260. The second housing 1220 may be provided to surround the second connector 1260. The second housing 1220 may protect the second connector 1260 from external impacts.

According to an embodiment, the second housing 1220 may include a cavity. At least a portion of the first O-ring 1170 may be accommodated in the cavity.

According to an embodiment, the second housing 1220 may extend in a longitudinal direction of the ultrasonic probe 20. The second housing 1220 may have an external shape suitable for a user to hold the ultrasonic probe 20.

According to an embodiment, one end of the second housing 1220 may be in contact with the first housing 1120, and the other end of the second housing 1220 may be in contact with the second coupler 1320.

According to an embodiment, the second housing 1220 may be detachably coupled to the first housing 1120. For example, the second housing 1220 and the first housing 1120 may be engaged with each other without a separate adhesive material. Accordingly, one end of the second housing 1220 may be separated from the first housing 1120 without applying excessive force. The ultrasonic probe 20 according to an embodiment is configured so that the first housing 1120 and the second housing 1220 are detachably coupled to each other, and thus, internal components (e.g., the acoustic module 1130) of the ultrasonic probe 20 may be physically accessed without causing damage to the ultrasonic probe 20.

A detailed description of a coupling method between the second housing 1220 and the first housing 1120 will be given with reference to FIGS. 8 to 10.

The second connector 1260 may be arranged in the second housing 1220. At least a portion of the second connector 1260 may be accommodated in the second housing 1220. According to an example, the second connector 1260 may be referred to as a frame.

According to an embodiment, the second connector 1260 may include a first end 1262 and a second end 1264. The first end 1262 of the second connector 1260 may be coupled to the first connector 1160, and the second end 1264 of the second connector 1260 may be coupled to the first coupler 1310.

According to an embodiment, the second connector 1260 may include a main body portion 1265, a first branch portion 1266, and a second branch portion 1267.

According to an embodiment, the first branch portion 1266 may be engaged with the first connector 1160, and the second branch portion 1267 may be engaged with the first coupler 1310.

According to an embodiment, the main body portion 1265 may be between the first branch portion 1266 and the second branch portion 1267. The main body portion 1265 may extend in a longitudinal direction of the second housing 1220. The first branch portion 1266 may extend in a direction from the main body portion 1265 toward the acoustic module 1130. The second branch portion 1267 may extend in a direction from the main body portion 1265 toward the coupler 1300.

According to an embodiment, the number of first branch portions 1266 may be equal to the number of first connectors 1160. For example, when there are two first connectors 1160, two first branch portions 1266 may be provided in the second connector 1260.

According to an embodiment, at least a portion of the main body portion 1265 may be arranged adjacent to the second housing 1220. The main body portion 1265 may include an inner hole. Because the inner hole is provided, a space in which other components are to be arranged in the second housing 1220 may be obtained. For example, though not separately shown in the drawings, when a separate processor is included in the ultrasonic probe 20, the processor may be arranged in the inner hole of the main body portion 1265.

According to an embodiment, the second connector 1260 may be engaged with the first connector 1160 to apply an external force. For example, when the first coupler 1310 applies, to the second connector 1260, an external force toward the rear of the ultrasonic probe 20, the second connector 1260 may apply, to the first connector 1160, an external force in the same direction as the external force toward the rear. For example, the force provided from the first connector 1160 may be provided to the first coupler 1310 via the second branch portion 1267, the main body portion 1265, and the first branch portion 1266.

The coupler 1300 may be arranged at the rear of the ultrasonic probe 20. The coupler 1300 may change relative positions of the second connector 1260 and the second housing 1220 with respect to each other. As described above, the coupler 1300 may include the first coupler 1310 and the second coupler 1320. The first coupler 1310 and the second coupler 1320 may be configured to be engaged with or separated from each other.

At least a portion of the first coupler 1310 may be provided in the second coupler 1320. One end of the first coupler 1310 may be connected to the second end 1264 of the second connector 1260. At least a portion of the first coupler 1310 may be engaged with the second connector 1260, and the first coupler 1310 may be detachably engaged with the second coupler 1320.

The first coupler 1310 and the second coupler 1320 may be detachably coupled to each other. The first coupler 1310 may be inserted into the second coupler 1320. A coupling between the first coupler 1310 and the second coupler 1320 is described with reference to FIG. 6. FIG. 6 is a schematic perspective view of a coupling between a first coupler and a second coupler, according to an embodiment.

Referring to FIG. 6, the first coupler 1310 and the second coupler 1320 may be engaged with each other by a screw method. Accordingly, the first coupler 1310 and the second coupler 1320 may be coupled to or disengaged from each other according to an intention of a user. For example, the first coupler 1310 has a screw shape as an external shape, and the second coupler 1320 has an external shape corresponding to the first coupler 1310, and thus, the first coupler 1310 may be inserted into the second coupler 1320. Accordingly, the first coupler 1310 and the second coupler 1320 may be engaged with each other without requiring a separate chemical substance.

According to an embodiment, when the first coupler 1310 and the second coupler 1320 are coupled to each other, the first coupler 1310 may apply an external force to the second connector 1260, or the second coupler 1320 may apply an external force to the second housing 1220. Accordingly, relative positions of the second connector 1260 and the second housing 1220 with respect to each other may be changed.

According to an embodiment, the first coupler 1310 and the second connector 1260 may be integrally provided. For example, in FIG. 3, it is shown that the first coupler 1310 and the second connector 1260 are separately provided and engaged with each other by a known method, but the first coupler 1310 and the second connector 1260 may be provided with the same configuration according to an embodiment. In this case, it may be interpreted that the first coupler 1310 and the second connector 1260 with the same configuration are engaged with the second coupler 1320.

According to an embodiment, the first coupler 1310 and the second coupler 1320 may be arranged at a critical engagement position when the first coupler 1310 is inserted into the second coupler 1320 by a certain height. When the first coupler 1310 and the second coupler 1320 are arranged at the critical engagement position, the first housing 1120, the second housing 1220, and the second coupler 1320 may be firmly coupled to form a contact surface with each other, and movements thereof may be limited. For example, when the first coupler 1310 and the second coupler 1320 are arranged at the critical engagement position, the second housing 1220 and the first housing 1120 form a contact surface with each other, and movement of the second housing 1220 is limited by the first housing 1120, and thus, movement in a forward direction may be interfered with. In this case, one end of the second housing 1220 may be connected to the first housing 1120, and the other end of the second housing 1220 may be connected to the second coupler 1320. According to an embodiment, when a user engages the second coupler 1320 with the first coupler 1310, and the second coupler 1320 and the first coupler 1310 reach the critical engagement position, engagement feedback for determining that the first housing 1120, the second housing 1220, and the second coupler 1320 are sufficiently coupled to each other may be provided to the user.

According to an embodiment, the coupler 1300 may be provided in the form of a strain relief. In this case, the first coupler 1310 may have a certain rigidity, and the second coupler 1320 may have a ductile property. For example, when the ultrasonic probe 20 is connected to the outside by wire, a wire connecting the ultrasonic probe 20 to the outside needs to be prevented from being damaged when a position and posture of the ultrasonic probe 20 is changed. In this case, the coupler 1300 may be provided in the form of a strain relief to prevent damage to the wire connecting the ultrasonic probe 20 to the outside. However, this is not limited to the aforementioned example.

Although not explicitly shown in FIGS. 3 and 4, the ultrasonic probe 20 may further include a second O-ring 1370. The second O-ring 1370 is described with reference to FIG. 7. FIG. 7 is a schematic perspective view of a first coupler and a second housing, according to an embodiment.

Referring to FIG. 7, the second O-ring 1370 may be between the second housing 1220 and the first coupler 1310. For example, the second housing 1220 may include a cavity arranged adjacent to the coupler 1300, and the second O-ring 1370 may be accommodated in the cavity of the second housing 1220.

According to an embodiment, the second O-ring 1370 may be in contact with the first coupler 1310. The second O-ring 1370 may not be in contact with the second coupler 1320. As described above, when the coupler 1300 is provided in the form of a strain relief, the second coupler 1320 may have a ductile property. That is, according to the present embodiment, when the first coupler 1310 having a certain rigidity, not the second coupler 1320 having a ductile property, is in contact with the second O-ring 1370, the second O-ring 1370 may be sufficiently compressed, and accordingly, sealing performance of the second O-ring 1370 may be improved.

Hereinafter, a method of manufacturing an ultrasonic probe according to an embodiment will be described with reference to FIGS. 8 to 10. The same reference numerals refer to the same components as those described above, and overlapping descriptions are omitted or simply provided.

FIG. 8 is a flowchart of a method of manufacturing an ultrasonic probe, according to an embodiment.

FIGS. 9 and 10 are diagrams for respective manufacturing operations of a method of manufacturing an ultrasonic probe, according to an embodiment.

Referring to FIG. 8, a method of manufacturing the ultrasonic probe 20, according to an embodiment, may include preparing a first module and a second module (S12), arranging a second connector to be accommodated in a second housing (S14), and engaging a first coupler and a second coupler with each other (S16).

In the preparing (S12), the first module and the second module may be prepared. According to an embodiment, the first module refers to an assembly including some of the components described above with reference to FIGS. 3 to 7 and may include the first housing 1120, the acoustic module 1130, the first connector 1160, the second connector 1260, and the first coupler 1310. The second module refers to an assembly including some of the components described above with reference to FIGS. 3 to 7 and may include the second housing 1220 and the second coupler 1320.

In the arranging (S14), the second connector 1260 may be provided in the second housing 1220. In the present operation, the second housing 1220 may be arranged to accommodate the second connector 1260. According to an embodiment, the second connector 1260 may be engaged with the first connector 1160. In addition, the second housing 1220 may accommodate the second connector 1260 and may be provided in a direction from a tail position (e.g., a rear end of the ultrasonic probe 20, where the coupler 1300 is arranged) toward a head position (e.g., a front end of the ultrasonic probe 20, where the acoustic module 1130 is arranged) of the ultrasonic probe 20. In the present operation, the second connector 1260 may be accommodated in the second housing 1220, and the first coupler 1310 may be exposed to the outside according to a position of the second housing 1220.

According to an embodiment, a state in which the second connector 1260 is provided in the second housing 1220 and the first coupler 1310 and the second coupler 1320 are not firmly engaged with each other may be referred to as a disengaged state.

In the engaging (S16), the first coupler 1310 and the second coupler 1320 may be engaged with each other. As an example of an engagement method, referring to FIG. 8, the first coupler 1310 and the second coupler 1320 may be engaged with each other by a screw engagement method.

According to an embodiment, the engaging (S16) may include applying, by the second coupler 1320, an external force to the second housing 1220. For example, in response to being engaged with the first coupler 1310, the second coupler 1320 may be moved in a forward direction of the ultrasonic probe 20 based on a position of the first coupler 1310. The forward direction may refer to a direction from the tail position to the head position of the ultrasonic probe 20. That is, the second coupler 1320 may push the second housing 1220 in the forward direction.

According to an embodiment, the engaging (S16) may include applying, by the first coupler 1310, an external force to the second connector 1260. For example, in response to being engaged with the second coupler 1320, the first coupler 1310 may be moved in a rearward direction of the ultrasonic probe 20 based on a position of the second coupler 1320. The rearward direction may refer to a direction from the head position to the tail position of the ultrasonic probe 20. That is, the first coupler 1310 may pull the second connector 1260 in the rearward direction.

According to an embodiment, in the engaging (S16), the second connector 1260 may pull the first connector 1160 in a direction toward the rearward direction. As described above, the second connector 1260 may receive, from the first coupler 1310, an external force in the rearward direction of the ultrasonic probe 20. Accordingly, the first connector 1160 physically connected to the second connector 1260 may receive the external force in the rearward direction of the ultrasonic probe 20.

According to an embodiment, in the engaging (S16), the first connector 1160 may pull the first housing 1120 in the direction toward the rearward direction. In this case, the first connector 1160 may apply an external force to the first housing 1120 without directly applying a force to the acoustic module 1130.

According to according to an embodiment, the engaging (S16) may include connecting the second housing 1220 to the first housing 1120. In this case, the first housing 1120 and the second housing 1220 may form a surface where the first housing 1120 and the second housing 1220 are physically in contact with each other, and because the first O-ring 1170 is arranged, a separation (or gap) that may occur between the first housing 1120 and the second housing 1220 may be prevented.

According to an embodiment, in the engaging (S16), when the first coupler 1310 pulls the first connector 1160 and the first housing 1120 in the direction from the head position to the tail position, the first housing 1120 and the second housing 1220 may be firmly engaged with each other. That is, when the first coupler 1310 and the second coupler 1320 are sufficiently engaged, even though the first housing 1120 is pulled by the first connector 1160, the first housing 1120 is fixed by the positions of the second coupler 1320 and the second housing 1220 and may no longer be moved.

According to an embodiment, a state in which the first coupler 1310 and the second coupler 1320 are firmly engaged, one end of the second housing 1220 is in contact with the first housing 1120, and the other end of the second housing 1220 is in contact with the second coupler 1320 may be referred to as an engaged state.

According to an embodiment, the method of manufacturing the ultrasonic probe 20 may include changing the first module and the second module from the disengaged state to the engaged state, and changing the first module and the second module from the engaged state to the disengaged state. That is, because the first module and the second module may be coupled to or disengaged from each other, when access to the internal components of the ultrasonic probe 20 is required, such as for repair of the ultrasonic probe 20, the first module and the second module may be easily separated such that physical access to the internal components of the ultrasonic probe 20 may be performed.

According to an embodiment, in order for the first housing 1120 and the second housing 1220 to be firmly coupled to each other, the first coupler 1310 and the second coupler 1320 need to be sufficiently engaged with each other (for example, when implemented as a screw type, the first coupler 1310 needs to be sufficiently inserted into the second coupler 1320). In this case, the first connector 1160 connected to the first coupler 1310 through the second connector 1260 may be connected to the first housing 1120 without being connected to the acoustic module 1130 (e.g., the lens portion 1132 of the acoustic module 1130). Accordingly, when the first housing 1120 and the second housing 1220 are coupled to each other, breakage or damage of the acoustic module 1130 may be prevented.

According to the related art, when an excessive force greater than or equal to a threshold value is applied to an ultrasonic probe, there is a concern that a component corresponding to an acoustic module may be damaged. In other words, applying a force of a certain level or more to an ultrasonic probe apparatus causes a risk of damage to an ultrasonic probe, and accordingly, an adhesive member is required for ultrasonic probes of the related art. Furthermore, due to the risk, it is difficult to switch individual components of the ultrasonic probes of the related art into an engaged state or a disengaged state.

However, according to an embodiment, even when a separate adhesive member (which may mean, for example, a known adhesive material) is not provided, the first housing 1120 and the second housing 1220 may be engaged with each other. As described above, even when the first coupler 1310 and the second coupler 1320 are sufficiently engaged with each other, damage to the acoustic module 1130 may be prevented. Accordingly, it is accepted that a force is applied by a user until the first housing 1120 and the second housing 1220 are sufficiently brought into close contact with each other. Therefore, even when a separate adhesive member is not provided, the ultrasonic probe 20 may be assembled. According to an embodiment, the ultrasonic probe 20 may be switched to an engaged state or a disengaged state according to a selection of the user.

The ultrasonic probe 20 according to an embodiment may have a disengaged state or an engaged state. The ultrasonic probe 20 may change from the disengaged state to the engaged state or from the engaged state to the disengaged state, as needed. Accordingly, when a close examination (inspection, repair, etc.) of individual components of the ultrasonic probe 20 is required, the individual components may be accessed by changing the ultrasonic probe 20 to the disengaged state without physical or chemical damage to the ultrasonic probe 20.

As an example, the ultrasonic probe 20 according to an embodiment may be applied to a regular repair and replacement service system for ultrasonic inspection equipment. According to a specific embodiment, when the ultrasonic probe 20 is implemented as a 2D array ultrasonic probe, the ultrasonic probe 20 may be provided in a normal state as long as the acoustic module 1130 included in the ultrasonic probe 20 normally functions. That is, even when another component (e.g., the second housing 1220) is damaged, an appropriate repair and/or replacement is performed such that the ultrasonic probe 20 may be prepared to be suitable for a normal state. Due to the characteristic of the ultrasonic probe 20 according to an embodiment being able to be switched to an engaged state or a disengaged state, the ultrasonic probe 20 may have excellent assemblability, and accordingly, a repair and replacement service provider for the ultrasonic probe 20 may easily disassemble, check, and reassemble the ultrasonic probe 20 at regular intervals (or when necessary).

As another example, in order to self-repair or check the internal state of the ultrasonic probe 20, a user may easily release the engaged state between the first housing 1120 and the second housing 1220 of the ultrasonic probe 20 and reassemble (or engage or couple) the first housing 1120 and the second housing 1220. Accordingly, the specific internal state of the ultrasonic probe 20 may be easily checked, and thus, the user may appropriately determine whether to repair or replace the ultrasonic probe 20. When individual components (for example, the first housing 1120 and the second housing 1220) of the ultrasonic probe 20 according to an embodiment of the disclosure are assembled, the acoustic module 1130 may be prevented from being deformed. For example, when the first coupler 1310 and the second coupler 1320 are engaged with each other, relative positions of the first housing 1120, the second housing 1220, the first connector 1160, and the second connector 1260 with respect to each other may be changed. In this case, the first connector 1160 to which an external force is applied from the second connector 1260 may not directly apply an external force to the acoustic module 1130, in particular, the lens portion 1132. That is, because the first connector 1160 has a structure of being connected to the inner surface of the first housing 1120, a phenomenon in which an external force is directly applied to the lens portion 1132 may be prevented. Therefore, there may be provided the ultrasonic probe 20 and the method of manufacturing the same, in which damage to the acoustic module 1130 during a manufacturing process may be further prevented.

As described above, the embodiments of the disclosure have been described with reference to the accompanying drawings. Those of ordinary skill in the art will understand that the disclosure can be implemented in forms different from the embodiments set forth herein without modifying the technical spirit or essential features of the disclosure. The embodiments of the disclosure are merely illustrative and should not be construed as limiting.

The invention claimed is:

1. An ultrasonic probe comprising:
a first housing;
a second housing;
an acoustic module at least partially arranged in the first housing and comprising a transducer and a lens portion, the transducer for converting an ultrasonic signal and an electrical signal, and the lens portion for changing a path of the ultrasonic signal;
a first connector arranged between the acoustic module and an inner surface of the first housing, connected to the inner surface of the first housing, wherein the first connector is not connected to the acoustic module;
a second connector at least partially arranged in the second housing and connected to the first connector; and
a coupler for changing relative positions of the second connector and the second housing with respect to each other,
wherein the first connector is configured to connect the second connector and the first housing to each other, wherein the first housing is coupled to the second housing,
wherein the second housing is between the first housing and the coupler,
wherein the coupler comprises a first coupler and a second coupler,
the second coupler being configured to be engaged with or separated from the first coupler
the first coupler is configured to connect the second connector to the second coupler and is insertable into the second coupler, and
when the first coupler and the second coupler are engaged with each other, the first coupler is configured to pull the second connector in a rearward direction with respect to the second housing,
wherein the ultrasonic probe comprises a head position where the acoustic module is arranged and a tail position where the coupler is arranged, and the rearward direction is a direction from the head position toward the tail position, and
wherein, when the first coupler and the second coupler are engaged with each other, the second connector is configured to pull the first connector in the rearward direction, and the first connector is configured to pull the first housing in the rearward direction.

2. The ultrasonic probe of claim 1, wherein the first housing and the second housing are physically in contact with each other without an adhesive member therebetween.

3. The ultrasonic probe of claim 2, wherein, when the second connector applies an external force to the first connector in a first direction, the first connector is configured to apply an external force to the first housing in the first direction.

4. The ultrasonic probe of claim 1, wherein the first connector and the first housing are integrally formed.

5. The ultrasonic probe of claim 1, wherein the second connector comprises a main body portion accommodated in the second housing and at least one branch portion extending from the main body portion,
the main body portion extends in a longitudinal direction of the second housing,
the branch portion is engaged with the first connector.

6. The ultrasonic probe of claim 1, wherein, when the first coupler and the second coupler are engaged with each other, the second coupler is configured to push the second housing in a forward direction, wherein the forward direction is a direction from the tail position toward the head position.

7. The ultrasonic probe of claim 6, wherein, when the first coupler and the second coupler are engaged with each other, an external force is applied to the second housing in the forward direction, and an external force is applied to the first housing in the rearward direction.

8. The ultrasonic probe of claim 7, wherein, when the first coupler is inserted into the second coupler, the first coupler and the second coupler are arranged at a critical engagement position, and
when the first coupler and the second coupler are arranged at the critical engagement position, the first housing and the second housing form a contact surface with each other, and movement of each of the first housing and the second housing is limited.

9. The ultrasonic probe of claim 8, wherein, when the first coupler and the second coupler are arranged at the critical engagement position, one end of the second housing is connected to the first housing, and the other end of the second housing is connected to the second coupler.

10. The ultrasonic probe of claim 1, further comprising: a first O-ring between the first housing and the second housing; and a second O-ring between the second housing and the first coupler.

11. The ultrasonic probe of claim 10, wherein the second O-ring is in contact with the first coupler without contacting the second coupler.

12. A method of manufacturing an ultrasonic probe, the method comprising:
preparing a first module and a second module, wherein the first module comprises a first housing, an acoustic module at least partially arranged in the first housing, a first connector arranged between the acoustic module and an inner surface of the first housing and connected to the inner surface of the first housing, a second connector connected to the first connector, and the second module comprises a second housing, the second connector at least partially arranged in the second connector, and a first coupler connected to the second connector, the first coupler configured to be engaged with or separated from a second coupler;
arranging the second connector to be accommodated in the second housing; and
engaging the first coupler and the second coupler to each other,
wherein the first connector is configured to connect the second connector and the first housing to each other, wherein the first housing is coupled to the second housing, wherein the first connector is not connected to the acoustic module,
wherein the second housing is between the first housing and the second coupler,
the first coupler is configured to connect the second connector to the second coupler and is insertable into the second coupler, and
when the first coupler and the second coupler are engaged with each other, the second connector is pulled in a rearward direction with respect to the second housing, by the first coupler,
wherein the ultrasonic probe comprises a head position where the acoustic module is arranged and a tail position where the coupler is arranged, and the rearward direction is a direction from the head position toward the tail position, and wherein, when the first coupler and the second coupler are engaged with each other, the second connector is configured to pull the first connector in the rearward direction, and the first connector is configured to pull the first housing in the rearward direction.

13. The method of claim 12, further comprising:

changing the first module and the second module from a disengaged state to an engaged state; and changing the first module and the second module from the engaged state to the disengaged state, wherein the engaged state is a state in which one end of the second housing is connected to the first housing and the other end of the second housing is connected to the second coupler, and the disengaged state is a state in which the first coupler and the second coupler are not engaged with each other.

14. The method of claim 12, wherein the engaging of the first coupler and the second coupler to each other further comprises:

applying, by the second connector, an external force to the first connector in a first direction; and applying, by the first connector, an external force to the first housing in the first direction.

* * * * *